(12) United States Patent
Dewaele et al.

(10) Patent No.: US 10,792,061 B2
(45) Date of Patent: Oct. 6, 2020

(54) MOTION AMPLIFIER FOR A STEERING MECHANISM OF A STEERABLE TOOL

(71) Applicant: Steerable Instruments NV, Sint-Denijs-Westrem (BE)

(72) Inventors: Frank Dewaele, De Pinte (BE); Cyriel Mabilde, Oudenaarde (BE); Bart Blanckaert, Eeklo (BE); Alain Kalmar, Ghent (BE); Lieven Maene, Knokke-Heist (BE)

(73) Assignee: Steerable Instruments NV, Sint-Denijs-Westrem (BE)

( * ) Notice: Subject to any disclaimer, the term of this patent is extended or adjusted under 35 U.S.C. 154(b) by 0 days.

(21) Appl. No.: 15/503,060

(22) PCT Filed: Dec. 8, 2015

(86) PCT No.: PCT/EP2015/078936
§ 371 (c)(1),
(2) Date: Feb. 10, 2017

(87) PCT Pub. No.: WO2016/091858
PCT Pub. Date: Jun. 16, 2016

(65) Prior Publication Data
US 2017/0273702 A1 Sep. 28, 2017

(30) Foreign Application Priority Data
Dec. 8, 2014 (EP) .................... 14196795

(51) Int. Cl.
*A61B 17/29* (2006.01)
*A61B 17/00* (2006.01)
*A61B 34/30* (2016.01)

(52) U.S. Cl.
CPC ........ *A61B 17/29* (2013.01); *A61B 2017/003* (2013.01); *A61B 2017/00314* (2013.01);
(Continued)

(58) Field of Classification Search
CPC .......... A61B 17/29; A61B 2017/00314; A61B 2017/00323; A61B 2017/291;
(Continued)

(56) References Cited

U.S. PATENT DOCUMENTS

| 7,410,483 B2 | 8/2008 | Danitz et al. |
| 2005/0107667 A1 | 5/2005 | Danitz et al. |

(Continued)

FOREIGN PATENT DOCUMENTS

| JP | H08224247 A | 9/1996 |
| JP | 2007509698 A | 4/2007 |

(Continued)

OTHER PUBLICATIONS

The International Search Report dated Mar. 23, 2016 for PCT/EP2015/078936.
(Continued)

*Primary Examiner* — Kathleen S Holwerda
*Assistant Examiner* — Brooke Labranche
(74) *Attorney, Agent, or Firm* — Amster, Rothstein & Ebenstein LLP

(57) ABSTRACT

The present invention relates to mechanical transmission system (100, MTS) having a proximal (20) and distal end (40), for a longitudinal steerable tube (500), which MTS (100) comprises a set of longitudinal members, LM, (110) arranged in a longitudinal direction around a fictive tube (180) maintained at an essentially constant circumferential and radial position with respect to the fictive tube (180) and being slidable relative to the fictive tube (180), and has a transmission bendable proximal part (134, TBPP), transmission bendable distal part (130, TBDP), and transmission shaft region, TSR (132) between the TBDP (130) and TBPP (134) wherein movements of the TBPP (134) are transmitted to the TBDP (130) along the TSR (132) by the LMs (110),
(Continued)

wherein the MTS (100) comprises a sub-region that is a transmission amplifier region, TAR, (135) in which the fictive tube (180) contains at least one plane-section (182) larger than that (184) of the TBDP (130).

12 Claims, 6 Drawing Sheets

(52) U.S. Cl.
CPC ............... *A61B 2017/00323* (2013.01); *A61B 2017/291* (2013.01); *A61B 2034/306* (2016.02)

(58) Field of Classification Search
CPC .......... A61B 2034/306; A61B 17/2918; A61B 17/2911; A61B 2034/301; A61B 34/71
See application file for complete search history.

(56) References Cited

U.S. PATENT DOCUMENTS

| | | | |
|---|---|---|---|
| 2006/0111615 A1* | 5/2006 | Danitz | A61B 1/00071 |
| | | | 600/141 |
| 2008/0015631 A1* | 1/2008 | Lee | A61B 17/062 |
| | | | 606/205 |
| 2008/0065116 A1 | 3/2008 | Lee et al. | |
| 2008/0111615 A1 | 5/2008 | Lee | |
| 2008/0262538 A1 | 10/2008 | Danitz et al. | |
| 2008/0294191 A1 | 11/2008 | Lee | |
| 2010/0076433 A1* | 3/2010 | Taylor | A61B 18/1445 |
| | | | 606/52 |
| 2010/0160735 A1* | 6/2010 | Bakos | A61B 17/3417 |
| | | | 600/141 |
| 2010/0168722 A1 | 7/2010 | Lee et al. | |
| 2010/0261964 A1 | 10/2010 | Danitz et al. | |
| 2010/0261971 A1 | 10/2010 | Danitz et al. | |
| 2010/0262075 A1 | 10/2010 | Danitz et al. | |
| 2010/0262161 A1 | 10/2010 | Danitz et al. | |
| 2010/0262180 A1 | 10/2010 | Danitz et al. | |
| 2011/0087071 A1 | 4/2011 | Danitz et al. | |
| 2011/0213347 A1 | 9/2011 | Lee et al. | |
| 2012/0245567 A1 | 9/2012 | Lee et al. | |
| 2012/0323070 A1 | 12/2012 | Danitz et al. | |
| 2013/0123783 A1 | 5/2013 | Marczyk et al. | |
| 2013/0219586 A1 | 8/2013 | Ihrke et al. | |
| 2013/0340559 A1 | 12/2013 | Danitz et al. | |

FOREIGN PATENT DOCUMENTS

| | | |
|---|---|---|
| JP | 2009538186 A | 11/2009 |
| JP | 2013039656 A | 2/2013 |
| JP | 2013103137 A | 5/2013 |
| JP | 2014064953 A | 4/2014 |
| WO | 2005044078 A2 | 5/2005 |
| WO | 2007139734 A2 | 12/2007 |

OTHER PUBLICATIONS

The Written Opinion of International Searching Authority dated Mar. 23, 2016 for PCT/EP2015/078936.

The International Preliminary Report on Patentability dated Nov. 10, 2016 for PCT/EP2015/078936.

\* cited by examiner

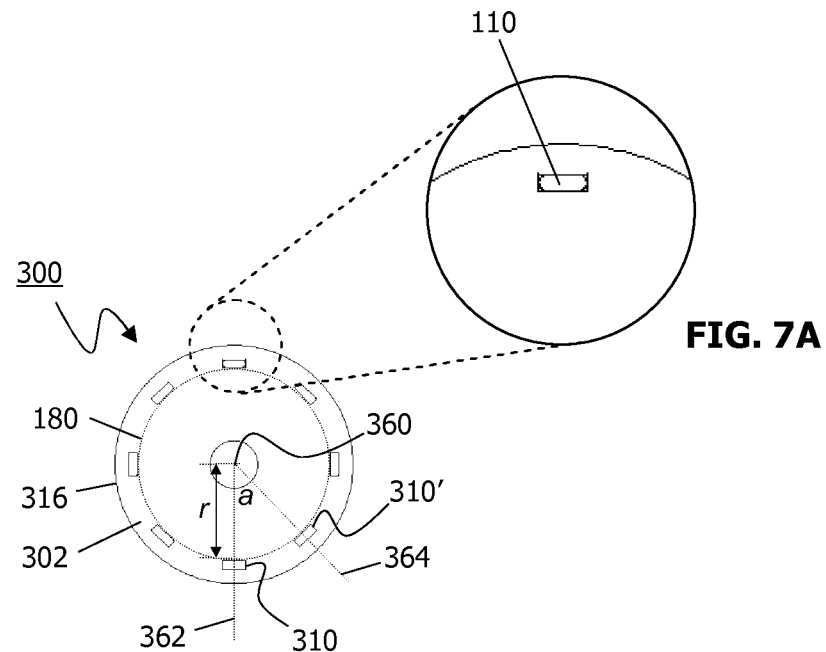
FIG. 7
FIG. 7A
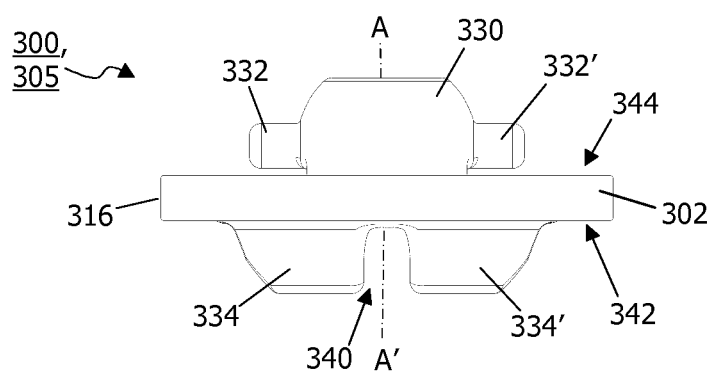
FIG. 8

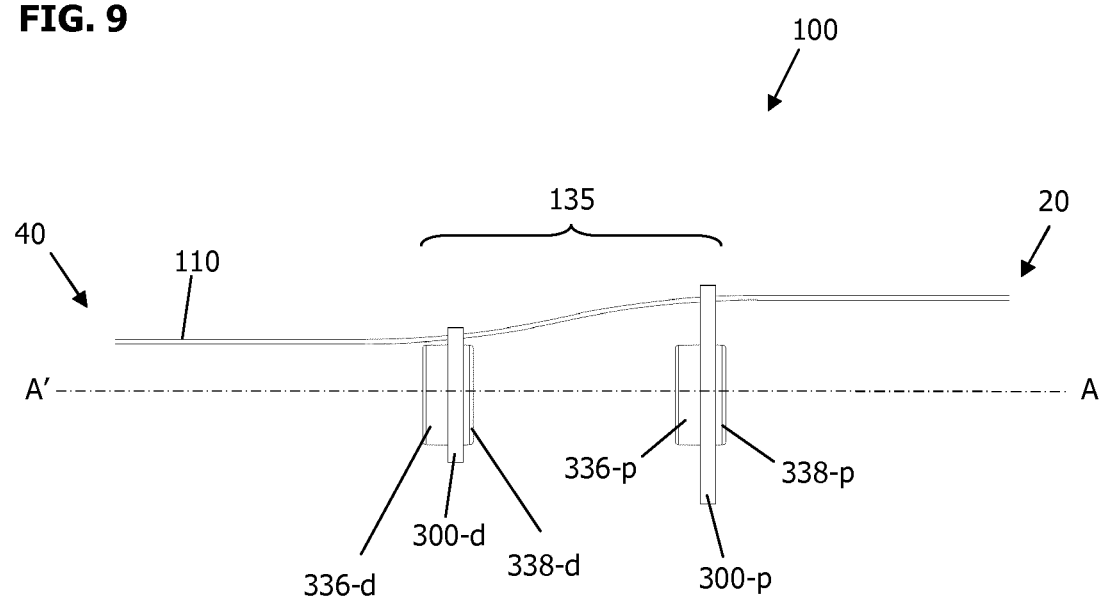
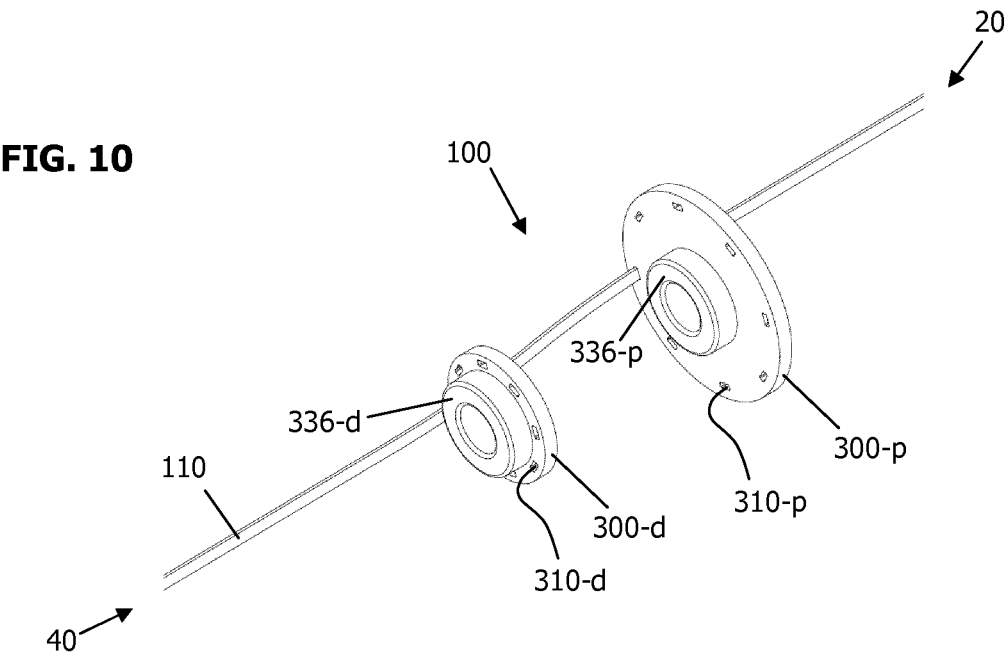

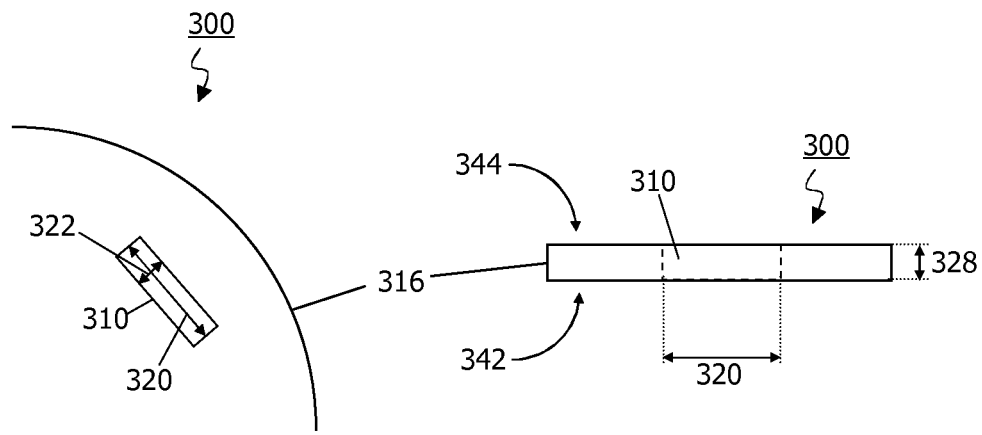
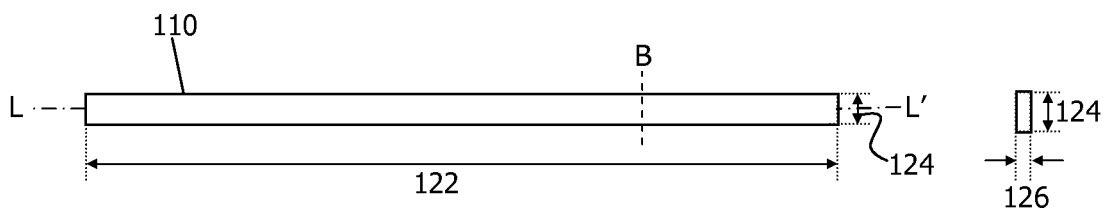
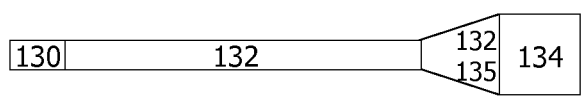
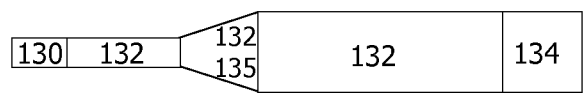
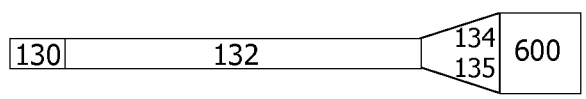

MOTION AMPLIFIER FOR A STEERING MECHANISM OF A STEERABLE TOOL

CROSS-REFERENCE TO RELATED APPLICATIONS

This application is a U.S. national stage entry under 35 U.S.C. § 371 of PCT International Patent Application No. PCT/EP2015/078936, filed on Dec. 8, 2015, which claims priority to European Application No. 14196795.0, filed on Dec. 8, 2014, the contents of which are incorporated herein by reference in their entirety.

BACKGROUND TO THE INVENTION

Surgery is characterized by a continuous search towards minimal invasiveness. Since the 1980s open surgery has been largely replaced by an endoscopic approach in which long instruments are inserted through trocars in a carbon dioxide-extended abdomen. Laparoscopic surgery, known for its validated benefits of shorter hospitalization, less postoperative pain and earlier recovery, is more demanding for the surgeon. Precise dissection, suturing and knot tying in minimal access surgery is an advanced skill. Especially when the suture line and the axis of the needle holder are unparallel this skill is difficult to master. Recent steps in the evolution towards minimal invasiveness are Single Port Surgery (SPS) and Natural Orifice Transluminal Endoscopic Surgery (NOTES). Both approaches result in a scarless healing. In SPS the instruments are inserted through one big trocar through e.g. the umbillicus.

A disadvantage of endoscopic surgery is reduced dexterity for the surgeon. This is mainly because of the fulcrum effect and the absence of wrist like movements at the tip of the instrument. Awareness of this disadvantage increases as more complex endoscopic procedures and single port surgeries (characterized by sword fighting of the instruments) are performed.

The fulcrum effect is explained by the long instruments that pivot at the level of the trocar inserted in the abdomen. A movement of the handle to the left is translated in a movement to the right at the effector (e.g. a pair of scissors). It is surprising to see how quickly a surgeon can adapt to these inversed movements.

The lack of wrist-like movements is more difficult to overcome. A state-of-the-art solution is provided by the surgical robot. In this master slave system the movements of the surgeon's hands at the console are transferred to fluent movements at the instrument's tip. This solution is quite expensive, leading to the development of cheaper hand instruments with an omni-directional articulated tip Most of the challenge is explained by the reduced dexterity. A conventional rigid laparoscopic instrument offers only 4 degrees of freedom (rotation, up/down angulations, left/right angulations, in/out movements).

To overcome this restriction in movements, various designs for steerable instruments have been developed. In its simplest form an articulated instruments consist of a prebent flexible tube sliding out of a rigid straight tube (uni-directional articulated instruments). This tip can only bend in one direction and cannot withstand an appropriate amount of lateral force. More advanced alternatives are instruments that allow bending movements of the tip in one plane. Because of the nature of the construction, a mostly stable tip is created. These bi-directional instruments need to be navigated to a point of interest by bending into one direction and then by turning the whole instrument around its own axis. This is not intuitive. True wrist movements are only possible with omni-directional systems. The omnidirectional articulated instruments consist mainly of a proximal and distal end, a proximal and distal bending part and an intermediate portion in between. Movement of the proximal end is transferred to a movement at the distal end. Examples are described in U.S. Pat. Nos. 7,410,483 and 8,105,350.

Similar to robotic surgery, omni-directional articulated instruments provide 7 degrees of freedom (axial rotation and deflection of the tip in two planes are added to the 4 DOF of conventional rigid instruments). A combination of up/down and left/right movements at the proximal side allows to reach any point at the distal effector side without the need for a rotation around its own axis.

The increased manoeuvrability is paid back by a serious decrease in tip stability. To solve this, hybrid solutions such as the Kymerax® system (Terumo) and Jaimy® system (EndoControl) compensate by using strong electrical motors to restore the tip stability.

Omni-directional articulated instruments offer, in comparison to robotic systems the advantages of low costs and tactile feedback.

A problem in the art of omni-directional articulated instruments lies in the operation by the surgeon using his wrist. While the human wrist joint is flexible insofar as it can adopt an almost infinite range of angles radial to the radius bone, the angular extent of bending is limited in all directions. In particular, gripping of the instrument by the fingers to retain a constant angle of entry means that the articulated ends are controlled almost exclusively by the wrist. A forward and backward wrist bending is typically limited to between 70 to 80 deg in adults, and side to side bending is even more limited. To attain a grip on the instrument and to main a constant angle of entry into the body, the wrist is pre-bent, meaning there less bending angular freedom available to the wrist in certain directions to control the instrument. Control the bending can be uncomfortable for the surgeon to attain angles at the extremities of motion, leading to strain, fatigue and hence a reduction in precision. It is an aim of the invention to overcome the problem of limited wrist travel in regard of steerable instruments.

Some Embodiments of the Invention

The present invention relates to a mechanical transmission system (100, MTS) having a proximal (20) and distal end (40), for a longitudinal steerable tube (500), which MTS (100):

comprises a set of longitudinal members, LM, (110) arranged in a longitudinal direction around a fictive tube (180) maintained at an essentially constant circumferential and radial position with respect to the fictive tube (180) and being slidable relative to the fictive tube (180), and has a transmission bendable proximal part (134, TBPP), transmission bendable distal part (130, TBDP), and transmission shaft region, TSR (132) between the TBDP (130) and TBPP (134) wherein movements of the TBPP (134) are transmitted to the TBDP (130) along the TSR (132) by the LMs (110), wherein the MTS (100) comprises a sub-region that is a transmission amplifier region, TAR, (135) in which the fictive tube (180) contains at least one plane-section (182) larger than that (184) of the TBDP (130).

The TAR (135) may be disposed with at least two of said LM guides (300, 305, 350, 350*a*). Consecutive plane sections of the fictive tube (180) in the TAR (135) may gradually increase in size in the distal (40) to the proximal (20) direction.

The TAR (135) may be located within the TSR or at least partially within the TBPP.

The MTS (100) may be further provided with a set of LM guides (300, 305, 350, 350a) configured to maintain the LMs (110) at the essentially constant circumferential and radial position and slidable with respect to the fictive tube (180).

Each LM guide (300, 305, 350, 350a) of the set may be formed from a single element. Each channel (310) of the set of channels may be formed from a single element.

Each LM guide (300, 305, 350, 350a) of the set may comprise a body provided with a set of discrete channels (310) each accommodating one or two LMs (110), which channels are arranged around the fictive tube (180).

Each channel (310) of the set of channels may be formed within the one piece body of an LM guide (300).

At least two LM guides in the set are articulated LM guides (305, 305a) may be tandemly arranged in the TBDP (130) and in the TBPP (134), each articulated with respect to an adjacent articulated LM guide (305, 305a), thereby supporting bending of the LMs (110) in the TBPP (130) and in the TBDP (134).

At least two LM guides (300, 305, 350, 350a) in the set disposed in the TAR (135) may be articulated LM guides (305, 305a) tandemly arranged in the TAR (135), each articulated with respect to an adjacent articulated LM guide, thereby supporting bending of the LMs (110) in the TAR.

The articulated LM guides (305, 305a) in the TBDP (130) or the TBPP (134) may be in pairwise mutual contact through a swivel joint.

The channels (310) of consecutive articulated LM guides (350a) may increase incrementally in distance from a central (A-A') axis of the MTS (100) in the proximal direction when the TAR (135) is in the TBPP (132).

At least two of the LM guides in the set are fixed LM guides (350) may be tandemly arranged in the TSR (132) and rotationally fixed with respect to each other.

The channels (310) of consecutive fixed LM guides (350a) may increase incrementally in distance from a central (A-A') axis of the MTS (100) in the proximal direction when the TAR (135) is in the TSR (132).

The MTS (100) may be configured to move the TBPP (134) and TBDP (130) omni-directionally.

The TBDP (130) may be configured for movement in at least two different intersecting planes responsive to the movements of the TBPP (134), and wherein the MTS (100) is further provided with an end effector (540) at the distal end of the TBDP (130) wherein the MTS (100) is configured such that the end effector (540) is rotationally fixed in relation to the TBDP (130), and the end effector is rotatable when the TBDP (130) is in a bent position, by a complementary rotation of the TBPP (134).

The fictive tube (180) in the TAR (135) may contain a truncated cone shape, the larger end of which is at the proximal (20) end.

The invention also relates to a steerable tube (500) comprising an MTS (100) as defined above.

BRIEF DESCRIPTION OF THE FIGURES

FIG. 7 is a plan view of an LM guide provided with a set of channels arranged around the fictive tube.

FIG. 7A is a detailed view of a channel of FIG. 7 into which a LM is disposed.

FIG. 8 is a side view of an articulated LM guide.

FIG. 9 is a side view of a TAR present in a transmission shaft region (TSR) of an MTS.

FIG. 10 is an isometric view of a TAR of FIG. 9

FIG. 11A is a plan view of a channel of an LM guide of the invention together with dimensional indications.

FIG. 11B is a side view of a channel of an LM guide of the invention together with dimensional indications.

FIG. 12A is a plan view of a LM together with dimensional indications.

FIG. 12B is a planar section of a LM at point B in FIG. 12A together with a dimensional indications.

FIG. 13 shows the TAR within the TSR and contacting the transmission bendable proximal part (TBPP).

FIG. 14 shows the TAR that is within the TSR.

FIG. 15 shows the TAR within the TBPP.

DETAILED DESCRIPTION OF INVENTION

Figure 1:
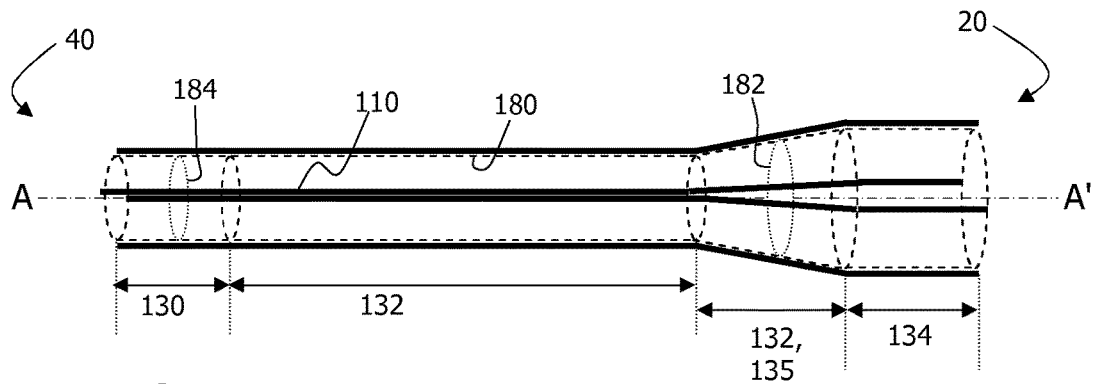
FIG. 1 is a schematic of a mechanical transmission system (MTS) of the invention having a set of longitudinal members (LMs) disposed around a fictive tube provided with transmission amplifier region (TAR).

Before the present method used in the invention is described, it is to be understood that this invention is not limited to particular methods, components, or devices described, as such methods, components, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. All publications referenced herein are incorporated by reference thereto. All United States patents and patent applications referenced herein are incorporated by reference herein in their entirety including the drawings.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The terms "distal" and "proximal" are used through the specification, and are terms generally understood in the field to mean towards (proximal) or away (distal) from the surgeon's side of the apparatus. Thus, "proximal" means towards the surgeon's side and, therefore, away from the patient's side. Conversely, "distal" means towards the patient's side and, therefore, away from the surgeon's side.

The present invention relates to a mechanical transmission system (MTS) for a steerable tool containing an amplifier region for amplifying actuating movements. The MTS contains a plurality of steering wires, known as longitudinal members, LM, herein, arranged around and contacting a fictive tube, which transmit movements from a transmission bendable proximal part, TBPP to a transmission bendable distal part, TBDP. A movement of the TBPP, transmitted via the LMs, results in a correspondingly larger movement of the TBDP. In the amplifier region, the size of the fictive tube towards the proximal end of the MTS is increased. For a small movement of the TBPP, the operator can obtain a larger travel distance at the TBDP. It finds particular utility in a surgical setting when the steerable tool is operated by digits of a single hand, and the available operating volume is limited. In a particular aspect, the LMs are disposed around the fictive tube and maintained in a fixed radial position with respect to a central axis of the MTS by LM guides which are mutually articulated at the bending end part of the mechanical transmission system (MTS) and hence of the steerable tool. The LM guide is disposed with a set of channels for holding the LMs in position. In the amplifier region, the channels are configured to guide the LMs from a smaller fictive tube towards the distal end of the MTS to a larger fictive tube towards the proximal end of the MTS.

The steerable tool is preferably longitudinal, meaning it is longer in one direction. It does necessarily not imply the steerable tool is linear, though a linear (straight) steerable tool is within the scope of the invention. The steerable tool may be straight or curved, for instance, having a C- or S-shape shaft region.

Typically, a steerable tool has a proximal end and distal end and contains an MTS. The steerable tool comprises a bendable distal part that moves responsive to actuation of the MTS at the proximal end. The BDP and BPP are sometimes known as a wrist. Actuation of the MTS at the proximal end induces a movement response in the BDP. The steerable tool is also provided with a shaft region, that may be essentially rigid or semi-rigid, one end of which is disposed with the BDP. The shaft region is longitudinal, meaning it is longer in one direction. It does necessarily not imply the shaft region is linear, though a linear (straight) shaft is within the scope of the invention. The shaft region may be straight or curved, for instance, having a C- or S-shape. To control BDP, steering wires which are known as longitudinal members (LMs) are used in the MTS. They control the BDP by pulling or pushing, hence the LM are able withstand tensile and compression forces. The MTS comprises a set of longitudinal members (LM) each having a proximal end and a distal end, arranged in a longitudinal direction around a fictive tube. The LMs in the set contact the fictive tube. The tip (distal terminal end) of the BDP should be able to move with equal ease in any direction i.e. there is no singularity. The movement response is proportion to the degree of actuation. There is an amplifier region, configured to change the shape of the fictive tube such as to reduce the radial distance of the LMs with respect to a central axis of the steerable tool in the distal direction. In particular, the AR is a region or zone in the steerable tool in which the size of the fictive tube increases from the distal end to the proximal end of the AR. The AR may be located in the SR and/or in the BPP. The AR may be located at least partially, preferably fully in the BPP. Preferably, the AR is located in the SR at the distal end. Preferably, the AR is located in the SR at the distal end and contacts the BPP.

The shaft region is preferably essentially rigid or semi-rigid, or may be flexible and become rigid or semi-rigid when co-operating with a rigid or semi-rigid exotube or outer tube. The shaft region is adjacent to the BDP. The shaft region may contact the BDP. The steerable tool may further be provided with a bendable proximal part (BPP) at the proximal end of the steerable tool. The BPP is adjacent to the shaft region i.e. the shaft region is disposed between the BDP and BPP.

Movement of the BPP actuates the MTS at the proximal end and induces a movement response in the BDP. Movement of BPP in different radial directions and to different bending degrees is transmitted using the MTS to the BDP, and results in a corresponding change in radial direction and/or degree of bending of the BDP. The steerable tool may be actuated at the proximal end using an electromechanical device connected directly to the MTS, for instance to two or more of the LMs, or each and every LM. Typically the LMs in the shaft region would be actuated. In such case, the tool may be devoid of a BPP.

Alternatively, robotic control may be realised by using an electromechanical device to actuate the BPP. The electromechanical device may be, for instance, a servo motor. Coupling to an electromechanical device would facilitate direct integration into a surgical robot.

The movement response of the BDP may be:
a change in degree of bending within a plane parallel to and contacting a central longitudinal axis of and extending from the shaft region,
a change direction of the bend within a plane perpendicular to and contacting a central longitudinal axis of and extending from the shaft region.

The combination of movements the steerable tool allows would normally facilitate a rotation of the shaft region that could be transmitted to BDP at its tip while the BDP is in a bent position.

The steerable tool may be a surgical instrument, such as, for instance, a laparoscopic instrument or an endovascular catheter. The invention can be used in an articulated instrument such as but not limiting to endovascular applications, surgical instruments, robotic tele-operated medical robotics or hand-held surgical tools and industrial applications.

The BDP is configured to move omni-directionally i.e. in any radial direction. BDP is preferably configured to move in any radial direction (about 360° with respect to central longitudinal axis (A'-A) of the shaft region). The BDP is preferably configured to move in at least two different planes (e.g. 3, 4, 5, 6, 7, 8 or more) disposed parallel to and contacting a central longitudinal axis (A'-A) of the shaft region. Preferably, the BDP is configured to move in an infinite number of different planes disposed parallel to and contacting a central longitudinal axis (A'-A) of the shaft region.

Similarly, the BPP is configured to move omni-directionally i.e. in any radial direction. BPP is preferably configured to move in any radial direction (about 360° with respect to central longitudinal axis (A'-A) of the shaft region). MTS is preferably configured to move the BPP in at least 8 different directions. The BPP is preferably configured to move in at least two different planes (e.g. 3, 4, 5, 6, 7, 8 or more) disposed parallel to and contacting a central longitudinal axis (A'-A) of the shaft region. Preferably, the BPP is configured to move in an infinite number of different planes disposed parallel to and contacting a central longitudinal axis of the shaft region.

The steerable tool may be provided with an end effector such as grip, pliers, cutting scissors and the like. The end effector is provided at the distal end of the steerable tool.

Furthermore it may be possible to rotate the distal tip of the instrument about its own axis even in a bent status. The steerable tool may be provided with an end effector at the distal end of the BDP wherein the MTS is configured such that the end effector is rotationally fixed in relation to the BDP, and the end effector is rotatable when the BDP is in a bent position, by a complementary rotation of the BPP. The end effector may be rotationally fixed in relation to the BDP by means of a lockable element configured to allow rotational adjustment of and to rotationally fix the end effector in rotational relation to the BDP.

The MTS as described herein has a proximal end and distal end. The proximal end and distal end correspond with those of the steerable tool. It has a central longitudinal axis. The distal end is provided with a transmission bendable distal part (TBDP) that that moves responsive to actuation of the MTS at the proximal end, and which moves the BDP of the steerable tool. The TBDP corresponds in position with the BDP. Movements of the TBDP are transferred to the BDP of the steerable tool. The proximal end is provided with a transmission bendable proximal part (TBPP). Movements by the user of the BPP of the steerable tool are transferred to the TBPP. The TBDP corresponds in position with the BPP. The TBPP actuates the MTS at the proximal end and induces the movement response of the TBDP that is transferred to the BDP of the steerable tool.

The MTS is also provided with a transmission shaft region (TSR) to be disposed within the corresponding shaft region of the steerable tool. The TSR is preferably essentially rigid or semi-rigid, or may become rigid or semi-rigid when co-operating with a rigid or semi-rigid exotube or outer tube.

The MTS contains a longitudinal sub-region that is a transmission amplifier region, TAR. It corresponds to the AR of the steerable tool and to the FTAR of the fictive tube described later below. The TAR is a region or zone in the MTS in which the size of the fictive tube increases from the distal end to the proximal end of the TAR. Typically, the fictive tube leaving the TAR at its proximal end retains the larger size at least until the proximal end of the MTS. The TAR may be located in the TSR and/or in the TBPP. The TAR may be located at least partially, preferably fully in the TBPP. Preferably, the TAR is located in the TSR at the distal end. Preferably, the TAR is located in the TSR at the distal end and contacts the TBPP. Preferably, the TAR is located in the TSR at the distal end. The TAR may be located exclusively in the TSR. The regions defined above preferably refer to the MTS in a neutral (non-actuated) mode.

The TAR contains at least one larger plane section compared with that at the TBDP. When comparing sizes of a plane section, the area of the plane section outer profile is compared. A plane section is typically a transverse cross-section perpendicular to the longitudinal central (A-A') axis of the fictive tube or MTS. Where the MTS has a circular profile, the size of the plane section refers to its outer diameter. As a consequence of the TAR, LMs in the TAR are set at a greater radial distance from the central axis of the MTS, compared with the LMs in the TBDP.

The size of plane sections in the TAR preferably reduces gradually from the TAR proximal end to the distal end. Hence, the TAR may have the shape of a truncated cone. The size of a plane section at the distal end of the TAR may be the same as the size of a plane section in the TBDP. The size of a plane section at the proximal end of the TAR may be the same as the size of a plane section in the TBPP.

The TBPP may be actuated manually or robotically. Robotic control may be realised by using an electromechanical device to actuate the BPP. The electromechanical device may be, for instance, a servo motor. This would facilitate direct integration into a surgical robot.

The TBDP is configured to move omni-directionally i.e. in any radial direction. TBDP is preferably configured to move in any radial direction (about 360° with respect to central longitudinal axis (A'-A) of the TSR). The TBDP is preferably configured to move in at least two different planes (e.g. 3, 4, 5, 6, 7, 8 or more) disposed parallel to and contacting a central longitudinal axis (A'-A) of the TSR. Preferably, the TBDP is configured to move in an infinite number of different planes disposed parallel to and contacting a central longitudinal axis (A'-A) of the TSR.

Similarly, the TBPP is configured to move omni-directionally i.e. in any radial direction. TBPP is preferably configured to move in any radial direction (about 360° with respect to central longitudinal axis (A'-A) of the TSR). MTS is preferably configured to move the TBPP in at least 8 different directions. The TBPP is preferably configured to move in at least two different planes (e.g. 3, 4, 5, 6, 7, 8 or more) disposed parallel to and contacting a central longitudinal axis (A'-A) of the shaft region. Preferably, the TBPP is configured to move in an infinite number of different planes disposed parallel to and contacting a central longitudinal axis of the shaft region.

The MTS may be provided with an end effector such as grip, pliers, cutting scissors and the like. The end effector is provided at the distal end of the steerable tool.

Furthermore it may be possible to rotate the distal tip of the MTS about its own axis even in a bent status. The steerable tool may be provided with an end effector at the distal end of the TBDP wherein the MTS is configured such that the end effector is rotationally fixed in relation to the TBDP, and the end effector is rotatable when the TBDP is in a bent position, by a complementary rotation of the TBPP. The end effector may be rotationally fixed in relation to the TBDP by means of a lockable element configured to allow rotational adjustment of and to rotationally fix the end effector in rotational relation to the TBDP.

The MTS comprises a set of longitudinal members (LMs) each having a proximal end and a distal end, arranged in a longitudinal direction around a fictive tube. The LMs of the set contact the fictive tube. The LMs are also known as steering wires. The LM as described herein has a proximal end and distal end.

Similar to the parts or regions of the MTS (TBDP, TSR, TBPP, TAR) the LM can be regarded as containing corresponding parts or regions. The distal end of the LM is provided with a LM bendable distal part (LMBDP) to be disposed in the TBDP of the MTS. The LM is provided with a LM shaft region (LMSR) to be disposed in the corresponding TSR of the MTS. The proximal end is provided with a LM bendable proximal part (LMBPP) to be disposed in the TBPP of the MTS. The LM is provided with a LM amplifier region (LMAR) to be disposed in the TAR of the MTS.

The LMAR is a region or zone in which the size of the fictive tube increases from the distal end to the proximal end of the LMAR. Typically, the fictive tube leaving the LMAR at its proximal end retains the larger size at least until the proximal end of the MTS. The LMAR may be located in the LMSR and/or in the LMBPP. The LMAR may be located at least partially, preferably fully in the LMBPP. Preferably, the LMAR is located in the LMSR at the distal end. Preferably, the LMAR is located in the LMSR at the distal end and contacts the LMBPP. The regions defined above preferably refer to the LM when the MTS is in a neutral (non-actuated) mode.

The distal ends of the LMs are maintained in fixed relation to each other in the MTS. The distal ends of the LMs, more preferably the distal terminal ends of the LMs, may be connected to a distal LM fixation element. Preferably, the distal LM fixation element maintains the LMs at their respective circumferential positions, for instance, it may maintain the distal terminal ends of the LMs in an annular ring. The distal LM fixation element may be, for instance, a disc or annulus disposed at the distal end of the MTS. The distal LM fixation element is preferably rigid.

Similarly, the proximal ends of the LMs, more preferably the proximal terminal ends of the LMs, may be maintained in fixed relation to each other in the MTS. The proximal ends of the LMs may be connected to a proximal LM fixation element. Preferably, the proximal LM fixation element maintains the LMs at their respective circumferential positions, for instance, it may maintain the proximal terminal ends of the LMs in an annular ring. The proximal LM fixation element may be a disc or annulus disposed at the proximal end of the MTS. The proximal LM fixation element is preferably rigid.

The LMs are slidable relative to each other, to the extent that movement is restricted by said LM fixation element(s). It is appreciated distal terminal ends of each LM in the set are maintained in fixed relation to each other (by the distal LM fixation elements), and the proximal terminal ends of each LM in the set are maintained in fixed relation to each other (by the proximal LM fixation elements) and hence the LMs do not slide relative to each other at the proximal and distal terminal ends. The application of force—pushing and/or pulling—at the proximal end of the MTS is transmitted via the LMs along the LMSR to the LMBDP which in turn causes movement of the TBPP e.g. by pulling or pushing the aforementioned fixation element(s). As the LMs slide over the FTAR, the distance with respect to the central axis of the MTS changes. LMs which move in the proximal direction are forced further away from the central axis of the MTS. LMs which move in the distal direction are forced closer to the central axis of the MTS.

The number of LM in the set may be at least two, for instance, 2, 3, 4, 5, 6, 7, 8, 9, 10, 11, 12, 13, 13, 14, 15, 16, 17, 18, 19, 20, 22, 24, 26 or more. For omni-directional steering, it is preferred that at least 4, more preferably at least 6 or 8, more preferably at least 6 or 8 LMs, even more preferably 18 to 22 LMs are present in the set.

An LM has a length, thickness and width (see FIGS. 10A and 10B). A width is the distance across a plane section in longer direction. A plane section is typically a transverse cross-section perpendicular to the longitudinal central (L-L') axis of an LM. A thickness is the distance across the plane section in shorter direction. The longer and shorter directions are perpendicular to each other. Where one of the sides of the plane section is straight, one direction is parallel to said straight edge. The width of the LM may be constant in the longitudinal direction. The thickness of the LM may be constant in the longitudinal direction. The thickness and width may be the same for instance, when the planar section is square or round. The length of the LM refers to the longitudinal length. Dimensions of an LM may depend on the diameter and length of the eventual steerable tool, and on the number of LMs utilised. As a general guidance, an LM may have a thickness in one direction of 40 µm, 50 µm, 60 µm, 80 µm, 100 µm, 200 µm, 200 µm, 400 µm or 500 µm, or a value in the range between any two of the aforementioned values. An LM may have a width of 80 µm, 100 µm, 120 µm, 140 µm, 160 µm, 180 µm, 200 µm, 300 µm, 400 µm, 500 µm, 600 µm, 700 µm, 800 µm, 900 µm, 1000 µm, 1100 µm, 1200 µm, 1300 µm, 1400 µm, or 1500 µm or a value in the range between any two of the aforementioned values. The skilled person would understand how to select a suitable thickness and width according to the diameter of the MTS. For a 10 mm diameter MTS, the preferred thickness is 280 µm to 320 µm, preferably about 300 µm, and the preferred width is 480 µm to 520 µm, preferably about width 500 µm in the LMBDP, LMSR and optionally LMBPP. The length of the MTS will depend on the length of the steerable tool and its application. The above preferred dimensions apply to MTS of 37-40 cm in length.

The LMs may be made from any suitable material having the appropriate tensile and compression properties and can be deduced by the person skilled in the art. Preferably the LMs are made from a non-compressible material. Examples include stainless steel or nitinol, beta titanium, spring steel, or polymer.

The LM may be made from a single strand of a material e.g. a single strip of stainless steel. Alternatively, it may be made from multiple strands of material tandemly connected.

The LMs are longitudinally arranged around the fictive tube. The LMs may be distributed evenly around the fictive tube e.g. the distance between adjacent LMs may be essentially the same. The LMs may distributed symmetrically around the fictive tube e.g. there may be a plane of symmetry about a longitudinal-cross section of the fictive tube. The LMs may be distributed unevenly around the fictive tube e.g. the distance between at least two pairs of adjacent LMs may be different.

The LM is preferably disposed essentially along the length of the MTS, and of the steerable tool. It spans the TBDP and extends into the TSR, and the TBPP where present.

The LMs are preferably arranged such that their longitudinal axes are mutually parallel. The LMs are preferably arranged such that their longitudinal axes are parallel to a longitudinal axis (A-A') of the fictive tube. The LMs are preferably arranged such that their longitudinal axes are parallel to a longitudinal axis of the longitudinal steerable tool.

The fictive tube as described herein has a proximal and a distal end, which corresponds to the proximal and distal ends of the steerable tool or MTS. The fictive tube has a central axis corresponding to the central axis of the steerable tool or MTS. The fictive tube is disposed along the length of the MTS.

The fictive tube is preferably longitudinal. It preferably has a circular plane section, a plane section being essentially perpendicular to a longitudinal axis and referring to the outer profile. Other plane sections are envisaged, however, such as oval. Preferably the shape of the plane section, e.g. circular or oval, is the same throughout the fictive tube, though transitioning, preferably gradual transitioning, between one or more shapes is within the scope of the invention. A central axis (A'-A) of the fictive tube is preferably coaxial with a central axis of the steerable tool. The fictive tube is preferably cylindrical. The fictive tube has diameter that is smaller than the diameter of the steerable tool at the corresponding position.

The distal end of the fictive tube contains a fictive tube bendable distal part (FTBDP) corresponding to the TBDP of the MTS, and to the BDP of the steerable tool. Preferably the FTBDP has a cylindrical shape in a non-bent configuration.

The fictive tube contains a fictive tube shaft region (FTSR) corresponding to the TSR of the MTS, and to the SR of the steerable tool. Preferably the FTSR has a cylindrical shape in a non-bent configuration. Preferably the FTSR has a constant size along the longitudinal length of the FTSR. The FTSR is proximal to the FTBDP.

The fictive tube contains a fictive tube bendable proximal part (FTBPP) corresponding to the TBPP of the MTS, and to the BPP of the steerable tool. The FTBPP is proximal to the FTSR. Preferably the FTBPP has a cylindrical shape in a non-bent configuration.

The LMs follow the longitudinal shape of the fictive tube. Where the fictive tube contains the fictive tube amplifier region (FTAR), for instance, the LMs follow the reduction in distance from the central axis in the distal direction. The LMs are maintained at essentially constant radial and circumferential position relative to the fictive tube. The LMs slide relative to the fictive tube in the FTSR, and in the FTBPP and FTBDP. The distal ends of the LMs, more preferably the distal terminal ends of the LMs are in fixed relation to the distal terminal end of the fictive tube. The proximal ends of the LMs, more preferably the proximal terminal ends of the LMs are in fixed relation to the proximal terminal end of the fictive tube.

The fictive tube contains a sub-region that is a fictive tube amplifier region (FTAR). It corresponds to the TAR of the MTS, and to the AR of the steerable tool. The FTAR is a region or zone in the fictive tube in which the size of the fictive tube increases from the distal end to the proximal end of the FTAR. The FTAR may be located in the FTSR and/or in the FTBPP. The FTAR may be located at least partially, preferably fully in the FTBPP. Preferably, the FTAR is located in the FTSR at the distal end. Preferably, the FTAR is located in the FTSR at the distal end and contacts the FTBPP. The FTAR is a longitudinal sub-region of the fictive tube, that contains at least one larger plane section compared with that at the FTBDP. When comparing sizes of a plane section, the area of the plane section outer profile is compared. A plane section is typically a transverse cross-section perpendicular to the longitudinal central (A-A') axis of the fictive tube or MTS. Where the fictive tube has a circular profile, the size of the plane section refers to its diameter. As a consequence of the FTAR, LMs arranged around and contacting the FTAR are set at a greater radial distance from the central axis of the fictive tube, compared with at the LMs arranged around the FTBDP.

The size of consecutive plane sections in the FTAR preferably reduces gradually from the FTAR proximal end to the distal end. Hence, the FTAR may have the shape of a truncated cone. The size of a plane section at the distal end of the FTAR may be the same as the size of a plane section in the FTBDP. The size of a plane section at the proximal end of the FTAR may be the same as the size of plane section in the FTBPP. The size of a plane section at the proximal end of the FTAR may be 1.5-3 times the size of a plane section at the distal end of the FTAR. Where the fictive tube has a circular profile, the diameter of a plane section at the proximal end of the FTAR may be 1.5-3 times the diameter of a plane section at the distal end of the FTAR.

As a general guidance for instruments such as surgical instruments, the FTAR may have a maximum diameter at the distal end of 0.1 cm, 0.15 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 1.9 cm or more, or a value between any two of the aforementioned values, preferably between 0.15 cm and 1.9 cm. The FTAR at the proximal end has a larger diameter compared with at the distal end, for instance, 10%, 20%, 40%, 60%, 80%, 100%, 150%, 200%, 250%, 300%, 350%, or 400% larger, or value in the range between any two of the aforementioned values. The increase in diameter in the proximal direction may be 0.1, 0.2, 0.3, 0.4, 0.5, 0.6 cm per 1 cm of longitudinal distance in the FTAR.

As explained, the LMs may be maintained in radial and circumferential alignment around the fictive tube using a set of LM guides described elsewhere herein.

The MTS is provided with a set of LM guides configured to support and maintain the arrangement of LMs around the fictive tube. There may be 2 to 30, more preferably 3 to 20 LM guides in the set. In particular, the set of LM guides maintain the set of LMs at a constant circumferential position on the fictive tube, and slidable relative thereto. In particular, the set of LM guides may axially rotationally constrain the LMs of the set, in particular at the TBDP and TBPP where present.

One or more LM guides of the set ("articulated LM guides" herein) may be articulated with respect to each other, particularly mutually pivoted, thereby supporting bending of the LMs, akin to a wrist joint. Articulated LM guides may be disposed in the TBDP and in the TBPP where present, corresponding to the BDP and the BPP of the steerable tool. In a MTS of 30 to 40 cm in length and a diameter of 6 mm to 8 mm, the TBDP may contain between 5 and 10 articulated LM guides. The distance between adjacent articulated LM guides may not exceed 12 mm, more preferably 10 mm when the LM guides are aligned in a straight line. This is to avoid buckling of the LMs.

One or more LM guides of the set ("fixed LM guides" herein) may be rotationally fixed with respect to each other, thereby maintaining a fixed (non-bending) path of the LM. Fixed LM guides may be disposed in the TSR, corresponding to the SR of the steerable tool, giving rise to an essentially rigid or semi-rigid TSR. In an MTS of 30 to 40 cm in length and a diameter of 6 mm to 8 mm, the TSR may contain between 13 and 17 fixed LM guides.

The TAR may comprise at least two LM guides of the set. Each LM guide may provide a discrete point of contact with each LM. For instance, in FIG. 5, the TAR (135) comprises a plurality of LM guides (350a, 350a', 350a''') each providing a discreet discrete point of contact with each LM in a longitudinal direction. Each LM guide is individual.

Where the TAR is disposed in the TSR, the TAR will contain a plurality of fixed LM guides giving rise to an essentially rigid or semi-rigid TAR. According to one aspect, the arrangement of LMs in the FTAR is realised by one or more fixed LM guides that across the length of the TAR bring the radial position of the LMs closer to the central axis of the MTS in the distal direction. In other words, the channels of consecutive fixed LM guides in the TAR increase incrementally in distance from the central axis of the MTS in the proximal direction. The fixed LM guides disposed in the TAR may constitute an overall truncated conical shape. The wider end of the cone is orientated in the proximal direction.

Where the TAR is disposed in the TBPP, the TAR will contain the articulated LM guides giving rise to an articulated TAR and hence articulated TBPP. According to one aspect, at least two LM guides in the set disposed in the TAR are articulated LM guides tandemly arranged in the TAR, each articulated with respect to an adjacent articulated LM guide, thereby supporting bending of the LMs in the TAR. The one or more, preferably at least 2 articulated LM guides in the TBPP across the length of the TAR bring the radial position of the LMs closer to the central axis of the MTS in the distal direction. In other words, the channels of consecutive articulated LM guides in the TAR (and hence in the TBPP) incrementally decrease in distance from the central axis of the MTS in the distal direction. The articulated LM guides disposed in the TAR (and hence in the TBPP) may constitute an overall truncated conical shape. The wider end of the cone is orientated in the proximal direction.

As mentioned above, the TSR may become rigid or semi-rigid when co-operating with a rigid or semi-rigid exotube or outer tube. In other words, the TSR may be flexible. Rigidly may be applied by inserting the TSR into a rigid or semi-rigid tube, or by clamping a rigid or semi-rigid tube around the TSR. Hence, articulated LM guides may be disposed in the TSR, corresponding to the SR of the steerable tool.

An LM guide comprises a body having a distal side and a proximal side, and an outer edge or surface connecting the distal and proximal sides.

For an articulated LM guide, the body is preferable substantially disc-shaped as shown, for instance, in FIGS. 7, 7A and 8. The body may be disposed with one component of a pair of components of a pivot joint on the proximal side of the body and the other component of the pair on the distal side of the body. Such a pivot joint may be a ball and socket joint. Adjacent articulated LM guides hence form a joint for mutual pivoting. The distance between adjacent discs may not exceed 12 mm, more preferably 10 mm when the discs are aligned in along a straight axis i.e. when the MTS is in a neutral position. This is to avoid buckling of the LMs. As a general guidance for instruments such as surgical instruments, a disc-shaped body present in the TBDP may have a diameter of 0.1 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 2 cm or more, or a value between any two of the aforementioned values, preferably between 0.2 cm and 1.6 cm. A disc-shaped body present in the TBPP typically has a larger diameter compared with in the TBDP, for instance, 10%, 20%, 40%, 60%, 80%, 100%, 150%, 200%, 250%, 300%, 350%, or 400% larger, or value in the range between any two of the aforementioned values. The outside edge of the body may have a thickness of 0.1 cm, 0.15 cm, 0.2 cm, 0.25 cm, or a value between any two of the aforementioned values, preferably between 0.1 cm and 0.2 cm. Where the TAR is present in the TBPP, the TBPP may comprise a plurality of articulated LM guides having a disc-shaped bodes having respective diameters decreasing gradually or stepwise from the proximal to the distal direction. The decrease may be 0.1, 0.2, 0.3, 0.4, 0.5, 0.6 cm per 1 cm of longitudinal distance in the TAR.

For a fixed LM guide, preferably one located in the TSR, the body may be substantially cylindrically shaped, the ends of the cylinder being the distal and proximal sides. As a general guidance for instruments such as surgical instruments, a cylindrical body may have a diameter of 0.15 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 2 cm or more, or a value between any two of the aforementioned values, preferably between 0.2 cm and 1.6 cm. The diameter of the articulated LM guide and the fixed LM guide may be the same. Where the TAR is present in the TSR, the aforementioned diameters may apply to a body in the TSR distal of the TAR. If the TSR extends proximal of the TAR, the cylindrical body typically has a larger diameter compared with distal of the TAR, for instance, 10%, 20%, 40%, 60%, 80%, 100%, 150%, 200%, 250%, 300%, 350%, or 400% larger, or value in the range between any two of the aforementioned values. The outside edge of the body may have a thickness of 0.1 cm, 0.15 cm, 0.2 cm, 0.25 cm, or a value between any two of the aforementioned values, preferably between 0.1 cm and 0.2 cm. The thickness of the outside edge of the body may be, for instance, 0.5 cm, 0.6 cm, 0.8 cm, 1 cm, 2 cm, 3 cm or more, or a value between any two of the aforementioned values, preferably between 1 cm and 3 cm.

While it is preferred that a plurality of tandemly arranged, fixed LM guides is present, it is within the scope of the invention that a single continuous fixed LM guide is disposed in the TSR, corresponding to the SR of the steerable tool; such embodiment applies in particular when the TAR is in the TBPP (see FIG. 15). Where the TAR is present in the TSR, the single continuous fixed LM guide is disposed in the TSR distal to the TAR (see FIG. 13), in particular when the TAR contacts the TBPP. Where the TAR is present in the TSR and the TSR extends proximal of the TAR (see FIG. 14), a second single continuous fixed LM guide is disposed in the TSR proximal to the TAR. A single continuous fixed LM guide may be up to 10 cm, 20 cm, 30 cm, 40 cm or 50 cm in length, or a value between any two of the aforementioned values. or a value between any two of the aforementioned values. It is appreciated that the single continuous fixed LM guide is not present in the TAR itself. A single continuous fixed LM guide can be formed by known processes such as extrusion. By tandemly arranged it is meant that the fixed LM guides are arranged end to end. Specifically, the proximal side of one fixed LM guide is in contact with the distal side of an adjacent fixed LM guide within the tandem arrangement. It is within the scope of the invention that there is one fixed LM guide.

Where the TAR is present in the TSR, the body of the fixed LM guide in the TAR is preferable substantially disc-shaped as shown, for instance, in FIGS. 5, 6, 9 and 10. Such TAR may contain a plurality of fixed LM guides, preferably more than 3, 5, or 7, more preferably between 5 and 10. The distance between adjacent disc-shaped bodies in such TAR may not exceed 12 mm, more preferably 10 mm. The body may be disposed with one component of a pair of components of a spacing joint on the proximal side of the body and the other component of the pair on the distal side of the body. A one component of a spacing joint is typically a protrusion (e.g. cylindrical protrusion) that provides a fixed distance between the adjacent fixed LM guide, and the other component is typically a reciprocating slot (e.g. cylindrical slot) for aligning the protrusion of an adjacent fixed LM guide. The spacing joint is fixed i.e. non-rotating and non-displacing. The spacing joint is preferably centred on the central axis of the MTS. The plane section of the spacing joint is preferably smaller than the plane section of the fictive tube. The spacing joint may be fixed using an adhesive.

As a general guidance for instruments such as surgical instruments, a disc-shaped body in the fixed LM guide of the TAR may have a maximum diameter at the distal end of 0.1 cm, 0.2 cm, 0.3 cm, 0.4 cm, 0.5 cm, 0.6 cm, 0.8 cm, 1 cm, 1.2 cm, 1.4 cm, 1.6 cm, 1.8 cm, 2 cm or more, or a value between any two of the aforementioned values, preferably between 0.2 cm and 2 cm. A disc-shaped body present in the fixed LM guide at the proximal end of the TAR typically has a larger diameter compared with at the distal end, for instance, 10%, 20%, 40%, 60%, 80%, 100%, 150%, 200%, 250%, 300%, 350%, or 400% larger, or value in the range between any two of the aforementioned values. The outside edge of the body may have a thickness equal to or up to 0.1 cm, 0.15 cm, 0.2 cm, 0.25 cm, 0.3 cm, 0.4 cm, 0.5 cm, 0.6 cm or a value between any two of the aforementioned values, preferably between 0.1 cm and 0.2 cm. Where the TAR is present in the TSR, the TAR may comprise a plurality of fixed LM guides having a disc-shaped bodes having respective diameters decreasing gradually or stepwise from the proximal to the distal direction. The decrease may be 0.1, 0.2, 0.3, 0.4, 0.5, 0.6 cm per 1 cm of longitudinal distance in the TAR.

Preferably, the body of the LM guide, either articulated or fixed is a one-piece element, e.g. is formed by moulding, extrusion or machining as one piece, avoiding the assembly of a plurality of elements. The body of the LM guide is also known as an integer part. The use of a one piece element eliminates the presence of crevices or air gaps around corners of the channels, through which an LM might pass and become lodged.

In particular construction (e.g. by injection moulding) of a single continuous solid body incorporating the channels that taper so as to change their radial distance would problematic. It would require the use of a plurality of cores, one for each channel, that are positioned at an angle. Withdrawing the cores at the same time as the mold is linearly separated would cause damage to the channels. Molding would require the angular removal of the cores that is distinct from the linear separation of the mold elements i.e. a two-step process. In the present invention, TAR is formed from a plurality of discrete LM guides either in the TSR or in the TBPP, each separately mouldered.

The body of the LM guide is provided with a set of channels. The number of channels in the set may be at least two, for instance, 2, 3, 4, 5, 6, 7, 8, 9, 10, 11, 12, 13, 13, 14, 15, 16, 17, 18, 19, or 20, or more. For omni-directional steering, it is preferred that at least 4, more preferably at least 6 or 8 channels are present in the set. The number of channel in the set of channels may be equal to the number of LMs in the set of LMs. A channel comprises a void space in the body of LM guide. A channel passes from the distal side to the proximal side of the LM guide body. A channel connects the distal side to the proximal side of the LM guide body. A channel preferably has a central axis from the distal side to the proximal side of the body that is parallel to the central axis (A-A') of the LM guide. Each and every channel of the set may be separate; in other words, the channels may not be interconnected. A channel can accommodate one, two, or more LMs, preferably only one LM. A channel is configured to constrain the LM, in particular to prevent radial movement with respect to the central axis of the body. A channel may be configured to constrain the LM, to prevent axial rotation, i.e. about the LM longitudinal (L-L') axis. A channel is dimensioned to facilitate longitudinal slidable movement of the LM therethrough. A channel may be closed or open. A channel may be formed from a single element. A channel provides a discrete point of contact for the LM. The channels are arranged around and contact the fictive tube as described elsewhere. The channels of the set are mutually spatially separated. A channel may contain a transverse profile that complements the profile of the LM to be accommodated. A transverse profile is perpendicular to the central axis of the channel. For instance, where the LM has a rectangular profile, the channel may contain a rectangular profile. It is appreciated that the channel profile need not precisely mirror the profile of the LM, for instance a race-track LM profile may be constrained by a rectangular channel.

A channel has a width, height and thickness (see FIGS. 11A and 11B). The thickness is equal to the thickness of the body. The height of the channel is the smallest distance from a base wall of the channel to a top wall of the channel measured in a straight line on a plane section of the channel perpendicular to the central axis. The width of the channel is the smallest distance between opposing channel side walls measured in a straight line on a plane section of the channel perpendicular to the central axis. The base wall, top wall and side walls are preferably planar.

For LM guides present in the TAR, the set of channels present in each LM guide may be adapted to guide the LM along an incline. When the channel thickness is too great, or the channel height is too small, the LM is restricted in its passage (see FIG. 16). One adaptation is to reduce the channel thickness (see FIG. 17); each channel may have a central axis from the distal side to the proximal side of the body that is parallel to the central axis (A-A') of the LM guide. Another adaptation is to change the geometry of the channel, for instance to introduce an inclination; each channel in the TAR may have a central axis from the distal side to the proximal side of the body that is inclined to the central axis (A-A') of the LM guide. This might be achieved using, for instance, a wedge-shaped channel (see FIG. 18) that has a reduced height on one side (e.g. on the distal side) of the LM guide that increases in the proximal direction towards a higher channel opening on the other side (e.g. on the proximal side) of the LM guide (that is compatible with a molding process). Alternatively the height of channel may be equally increased through the thickness of the LM guide which would accommodate an incline of the inserted LM (see FIG. 19). Alternatively the channel may have a concave shape, which would accommodate an incline of the inserted LM (see FIG. 20). The skilled person would understand how to determine the shape of the channel from the channel thickness, and the incline of the LM that must be accommodated.

The set of LM guides are tandemly arranged i.e. distal side of one LM guide faces the proximal side of an adjacent LM guide. An example of tandemly-arranged articulated LM guides is shown in FIGS. 2, 3, 5 and 6. The articulated LM guides in the set of LM guides are mutually (pairwise) articulated. Preferably, the articulated LM guides are in mutual (pairwise) contact. Preferably, an articulated LM guide contacts an adjacent LM guide using a pivot joint, such as a ball-and-socket type joint. The pivot joint allows pivoting of an articulated LM guide with respect to an adjacent articulated LM guide. The pivot joint may allow two degrees of freedom of movement with respect to an adjacent articulated LM guide i.e. roll and pitch. The pivot joint may or may not also allow relative rotation of adjacent articulated LM guides (i.e. yawing or axial rotation between adjacent articulated LM guides). Prevention of yawing can be achieved for instance, using a rotation limiter that might be a protrusion fixed on the body of one articulated LM guide that is received by a recess fixed on the body of an adjacent articulated LM guide (as shown, for instance, in FIG. 8); coupling prevents axial rotation of one LM guide relative to the adjacent LM guide.

The one or more fixed LM guides of the set of LM guides are mutually (pairwise) in fixed relation. They are preferably in fixed rotational relation. They are preferably in fixed distance relation. Preferably, the one or more fixed LM guides are in mutual (pairwise) contact.

The LM guides of the set are tandemly arranged such the circularly-arranged channels are in alignment, and each can receive one (or optionally two or more) LMs.

Preferably, the articulated LM guide is substantially disc-shaped, is provided with 10-20 channels each configured to accommodate only one LM, each channel containing a rectangular transverse profile the long side of the rectangle oriented to face a central axis of the LM guide, the channels being arranged around a fictive tube. The channel width is preferably 0.55 to 0.65 mm. The articulated LM guide preferably has an outer diameter of 0.9 to 1.1 cm, and a body thickness of 0.9 to 1.1 mm. The fictive tube in the TBDP preferably has an outer diameter of 0.75 to 85 cm.

Preferably, the fixed LM guide is substantially cylindrically-shaped, is provided with 10-20 channels each configured to accommodate only one LM, each channel containing a rectangular transverse profile, the long side of the rectangle oriented to face a central axis of the LM guide, the channels being arranged around a fictive tube. The channel width is preferably 0.55 to 0.65 mm. The fixed LM guide preferably has an outer diameter of 0.9 to 1.1 cm, and a body thickness of 1.5 to 2.5 cm. The fictive tube in the TSR preferably has an outer diameter of 0.75 to 85 cm.

Each channel is configured to constrain the LM to reduce or prevent axial rotation, and to maintain its radial position with respect to a central LM guide axis (A-A').

The steerable tool or MTS may be provided with an end effector, and configured such that the end effector is rotationally fixed in relation to the LMBDP, and the end effector is rotatable when the LMBDP is in a bent position, by a complementary rotation of the LMBPP. Hence, the steerable tool may be configured such that the end effector is rotationally fixed in relation to the BDP and the end effector is rotatable when the BDP is in a bent position, by a complementary rotation of the BPP. The rotationally fixed effector end may be realised by a permanent attachment to the tip of the LMBDP or BDP, for instance be welding or adhesive. Alternatively, the rotationally fixed end effector may be realised by a lockable revolute attachment to the tip of the LMBDP or BDP, in which the end effector is rotationally fixed in relation when the end effector is locked in position.

Reference is made in the description below to the drawings which exemplify particular embodiments of the invention; they are not at all intended to be limiting. It will be understood that the skilled person may adapt the device and substitute components and features according to the common practices of the skilled artisan.

FIG. 1 is a schematic of an MTS 100 of the invention having a proximal 20 and distal end 40, and a central longitudinal axis A-A'. The MTS 100 contains a transmission bendable distal part (TBDP) 130, a transmission shaft region (TSR) 132, and a transmission bendable proximal part 134 (TBPP) tandemly arranged from the distal end 40 to the proximal end 20. A transmission amplifier region (TAR) 135 is provided in the TSR 132.

Longitudinal members, LMs 110 are arranged around a fictive tube 180 having a central longitudinal axis (A-A') that is the same as the central longitudinal axis of the MTS 100. The LMs 110 are maintained at essentially constant radial and circumferential position relative to the fictive tube 180. The LMs 110 are slidable relative to the fictive tube 180. In the TAR 135, at least one plane section 182 is greater in size than a plane section 183 of the TBDP 130. The TAR 135 has a truncated conical appearance, the base of the cone pointing in the proximal 20 direction.

Figure 2:
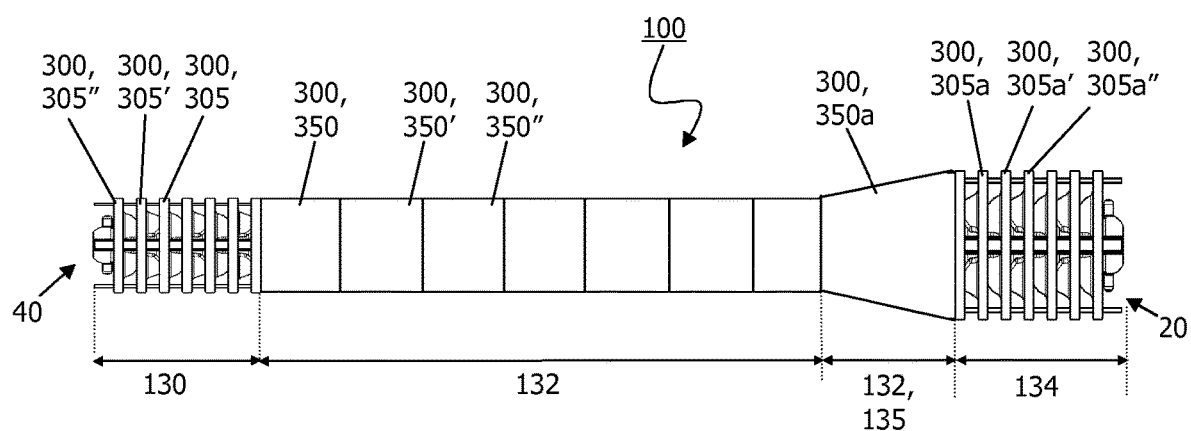
FIG. 2 depicts a plan view of an MTS of the invention provided with transmission amplifier region (TAR) whereby radial and circumferential position of the longitudinal member are maintained around the fictive tube by longitudinal member (LM) guides

FIG. 2 depicts a plan view of an MTS 100 having a proximal 20 and distal end 40, and transmission bendable distal part (TBDP) 130, a transmission shaft region (TSR) 132, and a transmission bendable proximal part (TBPP) 134 tandemly arranged from the distal end 40 to the proximal end 20. A transmission amplifier region (TAR) 135 is provided in the TSR 132. A set of LM guides 300 is indicated. The transmission shaft region (TSR) 132 is disposed with a plurality of fixed LM guides 350, 350', 350". The transmission amplifier region (TAR) 135, is disposed with a plurality of fixed LM guides 350a. The TBDP 130 is disposed with a plurality of articulated LM guides 305, 305', 305". The TBPP 130 is disposed with a plurality of articulated LM guides 305a, 305a', 305a". The LM guides maintain the LMs 110 at essentially constant radial and circumferential position relative to the fictive tube. The LMs 110 are slidable relative to the LMs guides 300.

Figure 3:
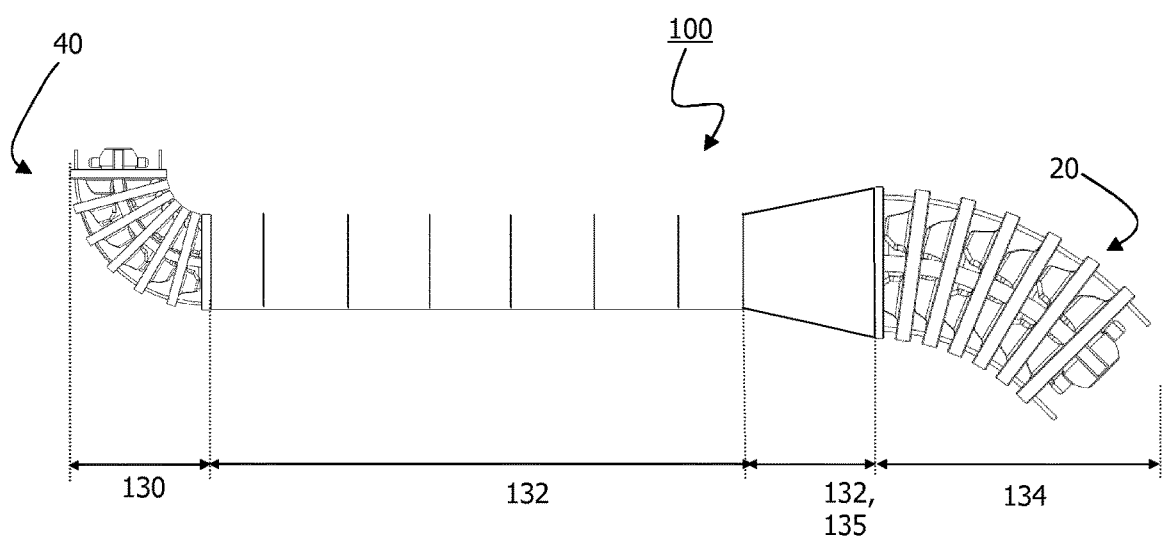
FIG. 3 depicts an actuated MTS of FIG. 2.

FIG. 3 depicts the MTS 100 of FIG. 2, in which TBPP 134 has been actuated by bending, the movement transmitted to the TBDP 130 along the TSR 132 by the MTS, which TBDP 130 bends responsively.

Figure 4:
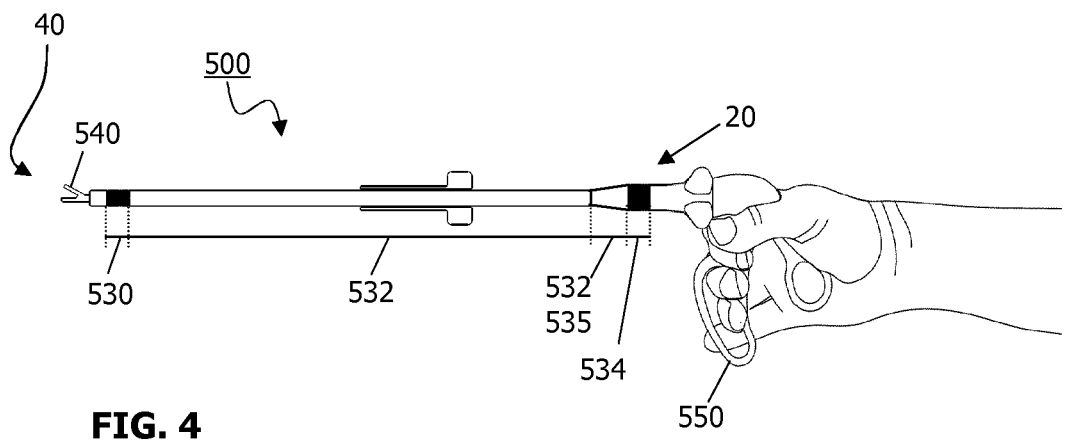
FIG. 4 depicts an isometric view of a steerable tool incorporating the MTS and TAR of the invention.

FIG. 4 is an isometric view of a steerable tool 500 incorporating the amplifier region of the invention. The steerable tool 500 has a proximal 20 and distal 40 end. The distal end 40 is provided with an end effector 540 that is a gripper, while the proximal end 20 is provided with a handle 550 to steer the tube and to control the gripper. Also indicated are the bendable distal part (BDP) 530, the shaft region (SR) 532 the bendable proximal part (BPP) 534, and the amplifier region (AR) 535 in the SR 532.

Figure 5:
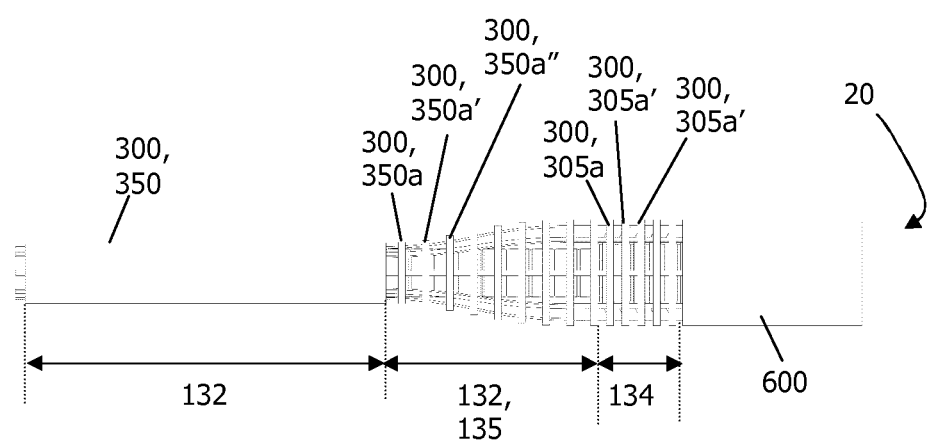
FIG. 5 is a plan view of the proximal end of an MTS.

FIG. 5 is a plan view of the proximal end 20 of an MTS 100. The transmission shaft region (TSR) 132 is disposed with a single fixed LM guide 350 in the TSR 132. The transmission amplifier region (TAR) 135, in the TSR 132 is disposed with a plurality of fixed LM guides 350a, 350a', 350a". These are spatially fixed relative to the fixed LM guide of the TSR and also with respect to each other. The TBPP 134 is disposed with a plurality of articulated LM guides 305a, 305a', 305a". The proximal end 20 of the TBPP 134 is provided with a handle 600.

Figure 6:
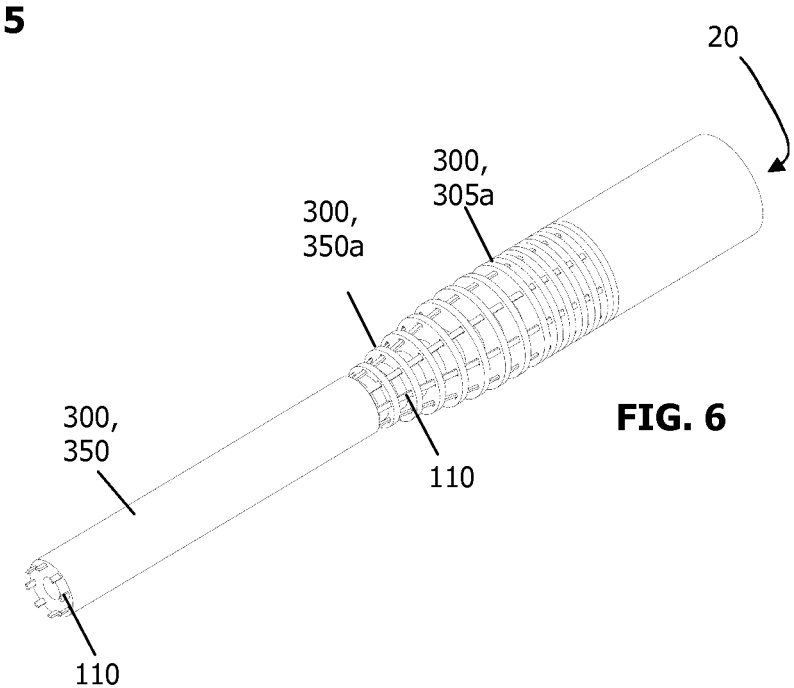
FIG. 6 is an isometric view of the MTS of FIG. 5.

FIG. 6 is an isometric view of the MTS 100 of FIG. 5.

FIG. 7 is a plan view of an LM guide 300 provided with a set of channels 310, 310' in the body 302 arranged around a fictive tube 180. Each channel 310 is in a fixed position relative to a central axis 360 of the fictive tube 180 or LM guide 300. As such the channel 310 retains an LM 110 at a constant radial position with respect to the central axis and a constant circumferential position on the fictive tube 180, and slidable relative thereto. The constant radial position of a channel 310 is marked by distance r between the central axis 360 and the channel 310, which distance r is constant within the LM guide 300. The constant circumferential position is marked by angle a between an arbitrary radial line 364 and a radial line to the channel 310, which angle a is constant within the LM guide 300; the radial lines are centred on the central axis 360.

FIG. 7A is a detailed view of a channel into which a LM 110 is disposed.

FIG. 8 is a side view of a LM guide 300 that is an articulated LM guide 305 having a disc shaped body 302, and a distal side 344 and a proximal side 342. A central axis (A-A') is indicated. The articulated LM guide 300 has a body 302 comprising at the distal side 344, one component of the pair of components that forms a pivot joint that is a dome protrusion 330, akin to the ball of a ball and socket joint. It further comprises at the proximal side 342, the other component of the pair of components that forms a pivot joint that is a reciprocating recess 340, akin to the socket of a ball and socket joint. Further indicated is a pair of rotation limiters (332, 332') fixedly connected to the dome protrusion 330, which are radial protrusions from said dome protrusion 330. These couple with a pair reciprocating slots 334, 334' fixedly connected to the receiving recess 340 of an adjacent articulated LM guide (not shown), to prevent mutual axial rotation of adjacent articulated LM guides.

FIG. 9 is a side view of a TAR 135 present in a TSR of an MTS 100. Two LM guides 300-d, 300-p at the distal (d) 40 and proximal (p) 20 end respectively of the TAR 135 are indicated constraining one LM 110. A central (A'-A) axis is shown. The LM guides 300-p, 300-d move the position of the LM 110 closer to the central axis in the distal direction 40. One component of a spacing joint that is a protrusion 336-d, 366-p and the other component that is a reciprocating slot 338-d, 338-p are shown on each LM guide 300-d, 300-p.

FIG. 10 is an isometric view of a TAR of FIG. 9, with channels 310-d, 310-p of distal LM guide 300-d, and proximal LM guide 300-p respectively, of the TAR 135. The radial distance of the channels 310-p of the proximal LM guide 300-p is clearly greater than the radial distance of the channels 310-d of the distal LM guide 300-d. One component of a spacing joint that is a protrusion 336-d, 366-p is shown on each LM guide 300-d, 300-p.

FIG. 11A is a plan view of a part of an LM guide 300 of the invention showing a channel 310 in detail together with dimensional indications that are the channel width 320 and channel height 322. The outer edge 316 of the LM guide 300 is also shown.

FIG. 11B is a side view of a part of an LM guide 300 of the invention showing a channel 310 in detail together with dimensional indications that are the channel width 320 and LM body thickness 328 which is equal to the channel thickness. The outer edge 316 of the LM guide 300 is also shown.

FIG. 12A is a plan view of a LM 110, together with dimensional indications that are the LM length 122 and LM width 124. A longitudinal axis (L-L') of the LM is also indicated.

FIG. 12B is a planar section of a LM at point B in FIG. 12A together with a dimensional indications that are the LM thickness 126 and LM width 124.

FIG. 13 shows a possible positioning of the TAR 135 that within the TSR 132 and contacting the TBPP 134.

FIG. 14 shows a possible positioning of the TAR 135 that is within the TSR 132.

FIG. 15 shows a possible positioning of the TAR 135 that is within the TBPP 134; a handle 600 is also shown.

Figure 16:
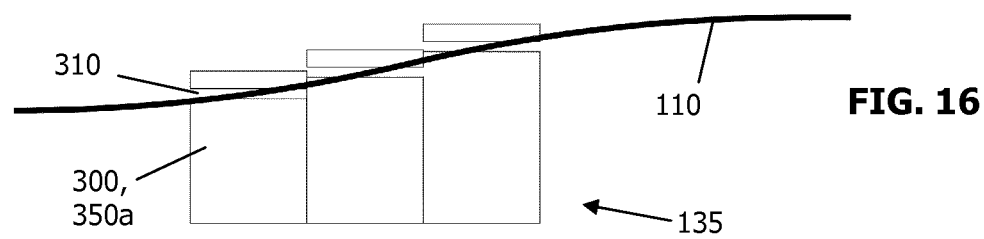
FIG. 16 shows a TAR disposed with a plurality of adjacently aligned fixed LM guides whereby the channels do not accommodate inclination of the LM.

FIG. 16 shows a TAR 135, disposed with a plurality of adjacently aligned fixed LM guides 350a that in combination displace the radial position of the LM 110 as a function of axial distance. The channels 310 in each LM guide 350a do not accommodate the inclination of the LM 310, and require modification.

Figure 17:
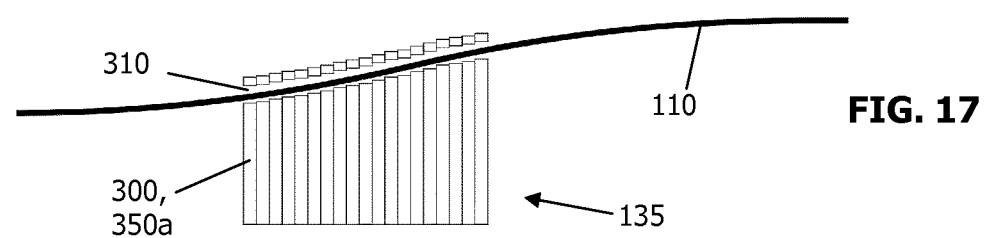
FIG. 17 shows a TAR disposed with a plurality of adjacently aligned fixed LM guides whereby the channels are sufficiently narrow to accommodate inclination of the LM.

FIG. 17 shows a TAR 135, disposed with a plurality of adjacently aligned fixed LM guides 350a that in combination displace the radial position of the LM 110 as a function of axial distance. The channels 310 in each LM guide 350a are sufficiently narrow to accommodate the inclination of the LM 310.

Figure 18:
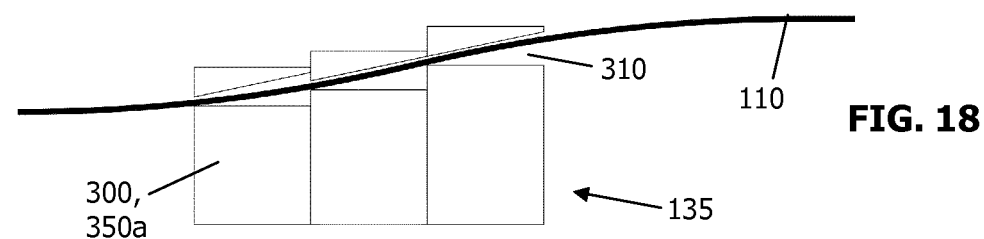
FIG. 18 shows a TAR disposed with a plurality of adjacently aligned fixed LM guide whereby the channels are wedge-shaped to accommodate the inclination of the LM.

FIG. 18 shows a TAR 135, disposed with a plurality of adjacently aligned fixed LM guides 350a that in combination displace the radial position of the LM 110 as a function of axial distance. The channels 310 in each LM guide 350a are wedge-shaped to accommodate the inclination of the LM 310.

Figure 19:
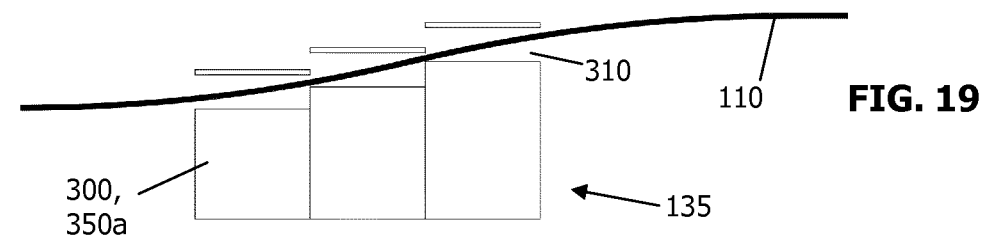
FIG. 19 shows a TAR disposed with a plurality of adjacently aligned fixed LM guides whereby the channels have increased channel height to accommodate the inclination of the LM.

FIG. 19 shows a TAR 135, disposed with a plurality of adjacently aligned fixed LM guides 350a that in combination displace the radial position of the LM 110 as a function of axial distance. The channels 310 in each LM guide 350a have increased channel height to accommodate the inclination of the LM 310.

Figure 20:
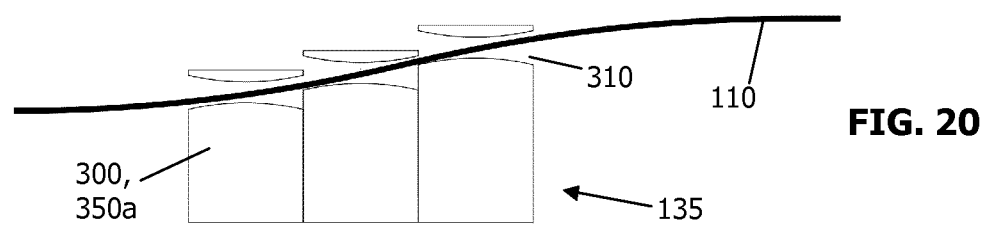
FIG. 20 shows a TAR, disposed with a plurality of adjacently aligned fixed LM guides whereby the channels have a "concave lens" shape to accommodate the inclination of the LM.

FIG. 20 shows a TAR 135, disposed with a plurality of adjacently aligned fixed LM guides 350a that in combination displace the radial position of the LM 110 as a function of axial distance. The channels 310 in each LM guide 350a have a "concave lens" shape to accommodate the inclination of the LM 310.

The invention claimed is:

1. A mechanical transmission system (100, MTS) having a proximal (20) and distal end (40), for a longitudinal steerable tube (500), which MTS (100): comprises a set of longitudinal members (110, LM) contacting and arranged in a longitudinal direction around a fictive tube (180) maintained at an essentially constant circumferential and radial position with respect to the fictive tube (180) and being slidable relative to the fictive tube (180), and has a transmission bendable proximal part (134, TBPP), transmission bendable distal part (130, TBDP), and transmission shaft region, (132, TSR) between the TBDP (130) and TBPP (134) wherein movements of the TBPP (134) are transmitted to the TBDP (130) along the TSR (132) by the LMs (110), wherein the MTS (100) comprises a sub-region that is a transmission amplifier region (135, TAR) in which the fictive tube (180) contains a truncated conical portion in which size of consecutive plane sections of the fictive tube (180) only gradually increase in the distal (40) to the proximal (20) direction, wherein the MTS (100) is further provided with a set of LM guides (300, 305, 350, 350*a*) configured to maintain the LMs (110) at the essentially constant circumferential and radial position and slidable with respect to the fictive tube (180), wherein the TAR (135) is disposed with at least two of said LM guides (300, 305, 350, 350*a*) within the truncated conical portion, wherein the TBDP (130) is configured for movement in at least two different intersecting planes responsive to the movements of the TBPP (134), wherein the MTS (100) is further provided with an end effector (540) at the distal end of the TBDP (130), wherein the MTS (100) is configured such that the end effector (540) is rotationally fixed in relation to the TBDP (130), and the end effector is rotatable when the TBDP (130) is in a bent position, by a complementary rotation of the TBPP (134), wherein each LM guide (300, 305, 350, 350*a*) of the set comprises a body provided with a set of discrete channels (310) each accommodating one or two LMs (110) which channels are arranged around the fictive tube (180) and wherein each channel (310) of the set of channels is formed from a single element in the TAR within the truncated conical portion.

2. The MTS (100) according to claim 1, wherein the TAR (135) is located within the TSR or at least partially within the TBPP.

3. The MTS (100) according to claim 1, wherein at least two LM guides in the set are articulated LM guides (305, 305*a*) tandemly arranged in the TBDP (130) and in the TBPP (134), each articulated with respect to an adjacent articulated LM guide (305, 305*a*), thereby supporting bending of the LMs (110) in the TBPP (130) and in the TBDP (134).

4. The MTS (100) according to claim 3, wherein the articulated LM guides (305, 305*a*) are in pairwise mutual contact through a swivel joint.

5. The MTS (100) according to claim 3, wherein the channels (310) of consecutive articulated LM guides (350*a*) increase incrementally in distance from a central (A-A') axis of the MTS (100) in the proximal direction and the TAR (135) is in the TBPP (132).

6. The MTS (100) according to claim 1, wherein at least two LM guides (300, 305, 350, 350*a*) in the set disposed in the TAR (135) truncated conical portion are articulated LM guides (305, 305*a*) tandemly arranged, each articulated with respect to an adjacent articulated LM guide, thereby supporting bending of the LMs (110) in the TAR truncated conical portion.

7. The MTS (100) according to claim 1, wherein at least two of the LM guides in the set are fixed LM guides (350) tandemly arranged in the TSR (132) and rotationally fixed with respect to each other.

8. The MTS (100) according to claim 7, wherein the channels (310) of consecutive fixed LM guides (350*a*) increase incrementally in distance from a central (A-A') axis of the MTS (100) in the proximal direction and the TAR (135) is in the TSR (132).

9. The MTS (100) according to claim 1, configured to move the TBPP (134) and TBDP (130) omni-directionally.

10. A steerable tube (500) comprising an MTS (100) as defined in claim 1.

11. The steerable tube (500) according to claim 10, wherein the distal end (40) is provided with an end effector (540) that is a gripper, and the proximal end (20) is provided with a handle (550) to steer the tube and to control the gripper.

12. A surgical robot comprising the MTS (100) according to claim 1.

\* \* \* \* \*